US010285772B2

(12) United States Patent
Oginski et al.

(10) Patent No.: US 10,285,772 B2
(45) Date of Patent: May 14, 2019

(54) SUPPORT JOINT FOR A CARRIER ARM OF A MEDICAL STAND DEVICE (71) Applicant: Ondal Medical Systems GmbH, Hünfeld (DE)

(72) Inventors: Stefan Oginski, Fulda (DE); Joachim Barton, Fulda (DE); Annika Euler, Hünfeld (DE)

(73) Assignee: Ondal Medical Systems GmbH, Hünfeld (DE)

( * ) Notice: Subject to any disclaimer, the term of this patent is extended or adjusted under 35 U.S.C. 154(b) by 6 days.

(21) Appl. No.: 15/525,016

(22) PCT Filed: Nov. 10, 2015

(86) PCT No.: PCT/EP2015/002255
§ 371 (c)(1),
(2) Date: May 5, 2017

(87) PCT Pub. No.: WO2016/074787
PCT Pub. Date: May 19, 2016

(65) Prior Publication Data
US 2017/0340408 A1  Nov. 30, 2017

(30) Foreign Application Priority Data

Nov. 10, 2014  (EP) .................................. 14003775

(51) Int. Cl.
A47F 5/00 (2006.01)
A61B 90/50 (2016.01)
(Continued)

(52) U.S. Cl.
CPC ............ *A61B 90/50* (2016.02); *A61G 12/002* (2013.01); *F16M 11/2014* (2013.01);
(Continued)

(58) Field of Classification Search
CPC ............... F16M 11/18; F16M 11/2014; F16M 11/2092; F16M 11/24; A61B 90/50; A61G 12/002
(Continued)

(56) References Cited

U.S. PATENT DOCUMENTS

2007/0080275 A1* 4/2007 Stachowski .............. A61B 8/00
248/323
2011/0315843 A1* 12/2011 Hung .................... F16M 11/041
248/279.1

FOREIGN PATENT DOCUMENTS

DE          103 14 156 B3     1/2005
DE     20 2011 005 203 U1    10/2011
DE        202011005203 U1 *  10/2011  ............. F16J 15/062

* cited by examiner

Primary Examiner — Todd M Epps
(74) Attorney, Agent, or Firm — Seed Intellectual Property Law Group LLP (57) ABSTRACT A carrier arm joint device for a carrier arm of a stand device for arranging in the operating room and for displacing a medical device held on the carrier arm is configured for setting a payload corresponding to a weight of the medical device to be taken up by the carrier arm. The device includes at least one pivot axis for mounting at least one strut of the carrier arm, respectively; and a support axis for supporting a lever configured to transmit forces holding the carrier arm between the strut and the carrier arm joint device A distance between the axes is adjustable within an adjustment range in order to set the payload; the size and/or the extent of the adjustment range is independent of the position of the pivot axis. It is possible to maximize the adjustment range and therefore the payload spectrum in a comparatively compact and structurally rigid joint. A carrier system and a stand device can include at least one such carrier arm joint device.

15 Claims, 4 Drawing Sheets (51) Int. Cl.
*A61G 12/00* (2006.01)
*G02B 7/00* (2006.01)
*F16M 11/20* (2006.01)
*F16M 11/24* (2006.01)
*F16M 13/02* (2006.01)
*F16M 11/04* (2006.01)
*F16M 11/06* (2006.01)

(52) U.S. Cl.
CPC ......... *F16M 11/2092* (2013.01); *F16M 11/24* (2013.01); *F16M 13/027* (2013.01); *G02B 7/001* (2013.01); *A61B 2090/5025* (2016.02); *F16M 11/043* (2013.01); *F16M 11/06* (2013.01); *F16M 2200/044* (2013.01); *F16M 2200/063* (2013.01)

(58) Field of Classification Search
USPC ..................................... 248/123.11
See application file for complete search history.

SUPPORT JOINT FOR A CARRIER ARM OF A MEDICAL STAND DEVICE

BACKGROUND

Technical Field

The present invention relates to a carrier arm joint device or a carrier system for holding and supporting a medical device with a predefined mass, wherein the payload of the carrier arm joint device is adjustable depending on the weight exerted by the medical device. Depending on the lever arm, the mass also exerts a torque on the carrier arm joint device. In particular, the present invention relates to a carrier arm joint device with single features of claim 1, as well as to a carrier system or stand device comprising single features of the respective independent claim, respectively, as well as the usage of such a carrier arm joint device on a medical stand device, in particular in an operating room.

Description of the Related Art

Stands, in particular, ceiling stands, as for example, ceiling supply units, monitor supports, or so-called spring arms or central axes, usually comprise one or more carriers arranged rigidly or in a way to be adjustable in height regarding a vertical position, by means of which an attached medical device may be moved and positioned, for example, in an operating room, in particular, also in an intensive care unit. On the stands supply units are usually attached, on which medical-electrical devices are arranged, for example, which will be supplied with the required media during surgery, for example. Devices may also be a (diagnosis) monitor or an illumination apparatus. The carriers or supply units are usually mounted to be rotatably and/or vertically adjustable and/or vertically pivotable around an at least approximately horizontally aligned axis. Depending on the function or design, the carriers may also be denoted as cantilevers, carrier arms or spring arms.

For such stands it is required to suspend the medical devices or terminals, wherein a counterforce has to be applied in a respective carrier which works against the weight of the device. The counterforce has to be adjusted depending on the mass of the device. Here, an adjustment may have to be performed for a maximum range of different weights or masses, and without limiting the freedom of movement of the carrier/carrier arm.

For balancing the medical device and to work against the mass thereof, a compression spring or a tension spring supported kinematics may be used, which is adapted as a parallelogram. Thus, the carrier arm comprises two struts which are arranged as a parallelogram and are mounted in two pivot axes with the ends thereof, respectively. The struts extend between two carrier arm joints that define two pivot axes being arranged one above the other, respectively. Here, the spring is here arranged on one of the struts and acts as energy storage and as a force generating component on the strut to accommodate the force components or torques resulting from the mass/weight of the medical device in the kinematics. The kinematics is adapted in a way that the spring arm is configured to hold or balance the medical device in the respective vertical position without the requirement to perform any additional settings on the spring arm. The carrier arm may be pivoted manually from the horizontal position about the (respective) pivot axis upwards or downwards and may be stopped at an arbitrary position, for example in a pivot range from +45° (upwards) and −50° (downwards). This kinematics may then be adjusted by using an integrated adjustment mechanics, in particular in the rear carrier arm joint. Such an adjustment mechanics will be explained in detail in FIGS. 1A, 1B.

BRIEF SUMMARY

It is a task of the present invention to provide a carrier arm joint or a device for a medical stand, by means of which the usage range may be enlarged and a broader payload spectrum may be defined. In particular, it is an object to provide at least one component of the carrier system configured at the factory by means of which not only especially large payloads, but also very small payloads may be set without having to make any design changes at the component. The object may also be to configure a connection between a carrier arm and a (pivot) joint for a parallelogram-like carrier arm or spring arm in a way that the strut of the carrier arm may be supported in different positions in a stable way in an adjustment arrange as large as possible, depending on the desired payload.

This task is achieved by a carrier arm joint device for a carrier arm of a stand device for arranging in the operating room and for displacing a medical device held on the carrier arm, wherein the carrier arm joint device is configured to set a payload corresponding to a weight of the medical device to be taken up by the carrier arm, comprising: at least one pivot axis for bearing at least one strut of the carrier arm, respectively; and a support axis to support a lever configured to transfer forces, in particular tension forces caused by (tension or compression) springs between the strut and the carrier arm joint device, wherein a distance between the axes (axial distance) is adjustable in order to set the payload within an adjustment range; and wherein the size and/or the extent of the adjustment range is independent of the position of the pivot axis. This way, a large adjustment range or a broad payload spectrum may be achieved.

The comparatively large adjustment range enables the usage of only one kind of spring as energy storage for different stands or lever arms lengths or masses or payload ranges. Here, a consistent setting of the spring force may be preset at the factory for several product types. A scaling of the spring force setting regarding specific payload ranges is thus no longer required. An user is able to individually set the required payload of the spring arm for the complete payload range on-site. This, last but not least, enables to readjust/set the carrier arm to comparatively small payloads also for a carrier arm with predefined comparatively high payloads.

Here, the distance between the axes (axial distance) defines the lever arm, with which a force exerted by the kinematics or a carrier arm spring engages with the carrier arm joint. Here, the distance between the axes may also define the relative angle of the lever. The present invention is based on the concept to configure the carrier arm joint device in a way that the axial distance may be minimized, in particular may converge to 0. Preferably, an especially large adjustment range is provided, which may extend to below at least one pivot axis.

In other words: The carrier arm joint device according to the invention may also result in a reduction of production variants for the manufacturer. An application planning may be simplified as carrier arms/spring arms of the same type does not have to be classified according to payload categories. In addition, the risk of confusing spring arms of the same type having specific payload ranges may be reduced.

The carrier arm joint device according to the invention may be configured to minimize the settable/adjustable payload by maximizing the adjustment range. The carrier arm joint device according to the invention may be configured to minimize the definable/adjustable payload by maximizing the axial distance.

Thus, a stand device is preferably a device for holding, fixing a position, and/or displacing at least one medical device that for medical purposes may be firmly mounted or positioned on a wall (in a wall bearing), or on a ceiling, or also on a floor of an operating room, or any other room; for example, a ceiling stand. The stand device thus may not be moved in a completely unrestricted way in the operating room, but may only be moved within a certain radius of action, in particular, relative to a fastening point or supporting point on a ceiling or a wall of the operating room. The stand device may be configured as a ceiling supply unit mounted on a ceiling, and include one or more supply units supported adjustably in position on one or two carrier arms. The stand device may also be adapted as a monitor support. The stand device may also be adapted as a so-called spring arm, in particular one that is mounted on a wall, and include a light, for example. Thus, a spring arm has a movable mechanics, in particular, one that is adjustable in height, which is capable of supporting a weight at different heights and is manually adjustable by using small operating forces (up to about 50 N). The stand device may also be adapted as a so-called central axis mounted, in particular on a ceiling, and comprise a plurality of carrier systems, each having at least one carrier on which a monitor or a light is mounted, for example. Preferably, the stand device includes at least two carrier arms.

Here, a medical device is preferably a supply unit by means of which the means for treating a patient and/or instruments for a surgeon and/or light, clean air, or other media required in the operating room can be provided. The medical device preferably includes some kind of control panel and/or some kind of display device, for graphically displaying patient data, for example.

An operating room may also be an examination room or an intensive care unit, that is a room for performing medical treatments or therapies.

Here, a pivot axis is preferably an axis around which a strut of a carrier arm can be verticality pivoted upwards or downwards. The pivot axis preferably extends in a horizontal plane, in particular orthogonal to an axis of rotation around which the carrier arm/spring arm or the carrier arm joint device may be mounted in the horizontal plane.

A support axis is here preferably an axis which is configured to transfer (compression or traction) forces from the carrier arm to the carrier arm joint, and to guide them into a casing of the carrier arm joint. The support axis may be displaceable and is supported on the carrier arm joint.

According to an exemplary embodiment, the pivot axis is arranged and/or dimensioned in a way relative to the support axis that the pivot and support axis do not overlap, in particular regarding the axial orientation thereof. Pivot and support axis may be arranged in the axial direction completely offset in relation to one another. This way, an adjustment range may be provided which extends over a maximum range of the joint device. The pivot axis may be arranged laterally of the adjustment range.

According to a variant, pivot and support axis are aligned parallel to each another.

According to an exemplary embodiment, the pivot axis is dimensioned and/or partitioned/divided in portions in a way that the relative position of the support axis in relation to the pivot axis may be set independent of the position of the pivot axis or of the lever, in particular the distance may be minimized. This way, a symmetric support may be realized, in particular on two outer axis portions spaced apart from one another as far as possible. The distance may be minimized independent of the position of the axis, thus an especially small payload may be set.

The axis portion may here preferably be a part of an axis which is arranged and supported separately from another part of the same axis. Here, the axis may be divided in two or more portions. Each portion may have the same function and is preferably aligned in the same direction.

According to an exemplary embodiment, the pivot axis is partitioned in at least two portions, adjacent or between which a cavity or a space is formed, in particular centered in the carrier arm joint device, wherein the adjustment range is arranged in the cavity, wherein the cavity is preferably configured to accommodate the lever or a bearing element/supporting element between the axis portions or adjacent to a respective axis portion. This way, a comparatively robust, large bearing element may also be arranged in a way that supporting forces may be applied in a symmetrical way.

Here the size of the supporting axis may be so short that the support axis may be positioned adjacent to the pivot axis or in a/the cavity between individual portions of the pivot axis, in particular in a casing of the carrier arm joint device. This way, an arrangement and support of the support axis may be enhanced, in particular in a cast casing.

According to an exemplary embodiment, the adjustment range is limited by a casing of the carrier arm joint device, in particular upwards and downwards. The length of the pivot axis is preferably smaller than the width of the casing. This way, a support axis may also be supported in the casing itself. This enables an especially robust arrangement.

According to an exemplary embodiment, the carrier arm joint device further comprises a bearing element/supporting element, in particular a bearing block, which defines the position of the support axis and may be coupled/is coupled to the lever, in particular by means of the support axis; and adjustment means to define/adjust the distance between the axis in the adjustment range, wherein the bearing element is coupled to the adjustment means, in particular in a form-fitting way. This way, the support axis may be exactly arranged in different positions in the adjustment range and may be supported independent of the respective position in a stable way. Here, the axial distance may be minimized preferably independent of the geometric configuration or dimension of the supporting element, thus it is possible to set an especially small payload.

Here, a bearing element is preferably a part by means of which an axis may be held and supported in different positions in a slidable way. The bearing element may ensure the mechanical interface between the axis and a component arranged on the carrier arm joint in a fixed position.

An adjustment means may preferably be a manually or mechanically adjustable mechanism by means of which a relative position of one of the axes in the carrier arm joint is adjustable/definable. The adjustment means may position the bearing element preferably in a form-fitting way, at least basically form-fitting. A mechanical interface between the adjustment means and the bearing element is basically preferably based on a form-fit configuration. The adjustment means may be adapted as setscrew, in a very simple our robust configuration. Optionally, also an engagement mechanism or rail with different discrete relative positions may be used.

According to an exemplary embodiment, the adjustment means are configured to guide the bearing element past the pivot axis and/or to position it in a/the cavity adjacent to the pivot axis in order to minimize the axial distance. This way, a comparatively small payload may be set, even for a comparatively large maximum payload value preset at the factory. And exact positioning of the support axis may be performed in the complete adjustment range, in particular also directly above the pivot axis with minimum lever forces. Here the adjustment means preferably extend in a direction orthogonal to the pivot axis past the pivot axis. This provides an advantageous kinematics, independent of the axial distance.

According to an exemplary embodiment, the carrier arm joint device, in particular a casing of the carrier arm joint device, defines a stop, on which the bearing element may abut in an arrangement with a minimum axial distance, wherein the stop is preferably arranged below the pivot axis. The bearing element may not abut/is not to abut on the pivot axis. There is thus no risk that the bearing element blocks the pivot axis. This way, a comparatively large, stable bearing block may be used.

According to an exemplary embodiment, the adjustment range extends between a top position of the bearing element and a bottom position of the bearing element up to below the (upper) pivot axis. The adjustment range or a corresponding cavity for accommodating a bearing element may extend past the pivot axis, thus the axial distance may be minimized.

According to an exemplary embodiment, at least one separate portion of the pivot axis is supported separately in the casing wall, and preferably also in a corresponding casing tongue, which is arranged on a side of the adjustment range, respectively. At least one portion of the pivot axis may be supported in a further casing wall or further casing tongue of the carrier arm joint device, wherein the casing walls preferably define an outer contour of the carrier arm joint device. The strut may thus be supported and guided using the respective tongues or protrusions between the casing wall and a casing tongue, whereby a high stability may be ensured.

According to an exemplary embodiment, the carrier arm joint device further comprises guiding means configured to guide a bearing element along a predefined movement path in the adjustment range, in particular along a straight line. The bearing element may be fixed in position by means of guiding means and/or may be guided along a, for example vertically aligned, positional line. The bearing element may be coupled to the guiding means and also to the adjustment means. Guiding means and adjustment means may extend in the same direction, in particular parallel to each another.

Here, a guiding means is preferably an element or part which is adequately dimensioned and supported, that is mounted and held in the carrier arm joint device, and by means of which support forces from a strut may be transferred to the joint device in different relative positions of a support axis. The guiding means may here also provide a bearing for the support axis or a supporting element, in particular a sliding bearing. The guiding means may be configured as a kind of carriage guide or a column guide, for example. Here, the guiding means may also take over a complete support of the bearing element, at least in the direction of force, in particular in the horizontal plane, and may thus also be denoted as supporting means.

According to an exemplary embodiment, the adjustment means are arranged between the guiding means and the pivot axis. This enables an advantageous stress distribution in the joint body or casing. The payload may be set in a comparatively direct way, as the adjustment means may be arranged directly adjacent to the support axis. It is further possible to prevent that vertical force components may be transferred to the guiding means. In an arrangement according to the state of the art it may not be avoided that due to a clamping of the bearing block with the guiding means also vertical force components may be transferred to the guiding means. However, this effect may be reduced or completely eliminated by a change of positions. In other words: Guiding means which are arranged behind the adjusting means as seen from the lever or from the spring arm, basically have only to be adapted for horizontal force components. A support in the vertical direction is not necessarily required. Vertical forces may already be accommodated by the adjustment means.

According to an exemplary embodiment, the adjustment means and/or the guiding means are aligned vertically/may be aligned vertically in a mounted arrangement of the carrier arm joint device, in particular parallel to an axis of rotation of the carrier arm joint device. This enables to align the kinematics of the arm in a comparatively simple way to the large adjustment range and may facilitate a (re-)processing of the joint device.

According to an exemplary embodiment, the carrier arm joint device is a cast part, in particular made from aluminum. This way, the carrier arm joint device may be configured as enhanced in function, as robust and in a material-saving way. In particular, a robust casing may be provided, in which the (upper) pivot axis or single axial portions may be mounted and supported. A large adjustment range is accomplished with an enlarged range, wherein support axis forces may be transferred to the casing, in particular by using a bearing block and a/the guiding bolt. A cast casing may provide a sufficiently rigid structure hereto. However, a welded construction would have to comprise a plurality of welding seems and reinforcements and would only be realized as a comparatively complicated part.

Aluminium is the preferred material. Optionally also zinc or steal or brass may be used, in particular for a zinc die-cast part or a steel die-cast part or a brass die-cast part. Depending on the requirements, the materials may be selected regarding strengths, robustness, bearing load or costs, for example.

Advantageously, the casing of the carrier arm joint device comprises a second stop, which defines an abutment plane opposite to the stop, on which the bearing element may abut in a minimum axial distance. Here, the bearing element comprises a bearing extension which protrudes from a central part of the bearing element in a direction opposite to the at least one pivot axis, thus the support axis is positioned in its position at a maximum distance from the at least one pivot axis in the region of the abutment plane. Here, the abutment plane is positioned at the maximum distance from the at least one pivot axis in a direction defined by the adjustment range.

The task mentioned above is also achieved by a carrier arm joint device for a carrier arm of stand device for arranging in the operation room and for displacing of the medical device held on the carrier arm, wherein the carrier arm joint device is configured for setting a payload corresponding to a weight of the medical device to be taken up by the carrier arm, comprising: at least one pivot axis for bearing at least one strut of the carrier arm, respectively; a support axis for supporting a lever configured to transfer forces holding the carrier arm between the strut and the carrier arm joint device; wherein a distance between the axes is adjustable within an adjustment arrange in order to set the payload; wherein the size and/or extension of the adjustment range is independent of the position of the pivot axis, and wherein the pivot axis is arranged and/or dimensioned in relation to the support axis in a way that the pivot and support axis do not overlap, in particular relating to the axial orientation thereof, and wherein the pivot axis is partitioned in at least two portions adjacent or between which a cavity or a space/cavity volume is formed, in particular centered in the carrier arm joint device, wherein the adjustment range is positioned in the cavity, further comprising: a bearing element/support element, in particular bearing block, which is supported on the support axis and is couplable/coupled to the lever; and adjustment means for setting the distance between the axis in the adjustment range, wherein the bearing element is coupled to the adjustment means, wherein the cavity is preferably adapted to partly accommodate the lever between the axial portions or adjacent to a respective axial portion, and wherein the carrier arm joint device, in particular a casing of the carrier arm joint device, defines a stop, on which the bearing element may abut in an arrangement with a minimum axial distance, wherein the stop is preferably arranged below the pivot axis. This results in previously described advantages.

The task mentioned above is also achieved by a carrier system for a stand device for arranging in the operation room and for displacing of a medical device having a predefined mass, comprising at least one carrier arm to hold the medical device with at least one strut mounted in one of the pivot axes, respectively, wherein a/the strut is additionally supported in the support axis by using a lever, preferably a parallelogram-style carrier arm having to struts being arranged preferably parallel to each other one above the other in the direction of the longitudinal axis of the carrier arm; and at least one carrier arm joint device with at least one pivot axis and with the support axis, wherein the support axis may be displaced and positioned in relation to the pivot axis in an adjustment arrange in order to set a payload of the carrier arm joint device in relation to the mass to be held, in particular a carrier arm joint device according to the invention; wherein a/the strut of the carrier arm is mounted on at least one portion on the pivot axis adjacent to the adjustment range or adjacent to a cavity defined by the carrier arm joint device, wherein the support axis is arranged and may be arranged in different positions within the adjustment range, wherein the pivot axis is spatially decoupled from the adjustment range. This results in previously described advantages.

The carrier system may comprise a further joint opposite to the carrier arm joint device, where at least one strut, in particular an end of the at least one strut, and the medical device are fastened.

According to an exemplary embodiment, a/the strut of the carrier arm is supported in two separate portions of the pivot axis, wherein the portions are supported in a casing of the carrier arm joint device respectively, wherein the adjustment range or the cavity is limited by the casing laterally outside. This way, an particular stable arrangement may be ensured despite of a maximum size adjustment range.

According to an exemplary embodiment, the carrier arm is adapted as a parallelogram-like carrier arm, wherein the carrier arm joint device defines two pivot axes for a strut of the carrier arm, respectively, wherein the support axis is arranged above the two pivot axis and the axial distance between the support axis and one of the upper pivot axis may be minimized in order to set the minimum payload. Due to the position of the support axis in relation to one or both struts, the leverage and thus the payload may be set.

The task mentioned above is also achieved by a stand device for arranging in the operation room and for displacing a medical device in the operating room, comprising at least one carrier arm joint device according to the invention and/or at least one carrier system according to the invention, wherein the at least one medical device comprises a predefined mass and is held in a predefined distance to the carrier arm joint device on a carrier arm of the carrier system, in particular on an end of the carrier arm, wherein the carrier arm joint device is set to a payload corresponding to a weight of the medical device to be taken up by the carrier arm, wherein a support axis of the carrier arm joint device is arranged/arrangeable independent of the position of a pivot axis of the carrier arm joint device in relation to the pivot axis, in particular in an adjustment range spatially separated from the pivot axes. This results in previously described advantages.

The task mentioned above is also solved by using a carrier arm joint device to set a payload of the medical carrier system, in particular a carrier arm joint device according to the invention, wherein a support axis of the carrier arm joint device is arranged in an adjustment range, which extends in relation to the at least one pivot axis of the carrier arm joint device in a way that the support axis is arrangeable spatially independent of the position of the pivot axis, in particular optionally adjacent or above are below the pivot axis, preferably laterally offset to the pivot axis.

BRIEF DESCRIPTION OF THE SEVERAL VIEWS OF THE DRAWINGS

The invention will be explained in greater detail in the following figures based on an exemplary embodiment. Illustrated are.

When describing the following Figures, for reference numbers that are not explicitly explained in a Figure, reference is made to the other Figures.

DETAILED DESCRIPTION

Figure 1A:
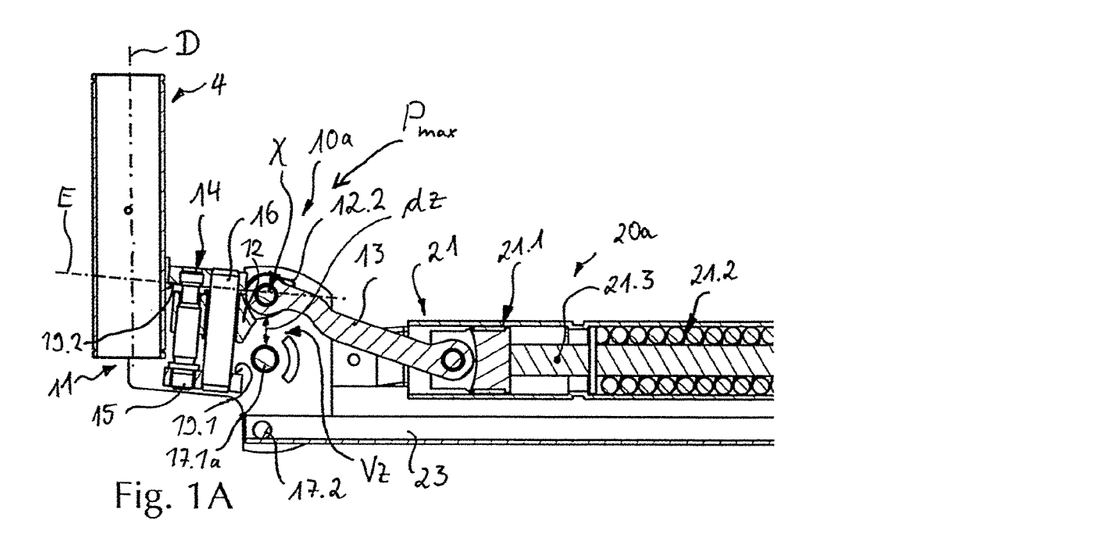
In FIG. 1A, 1B in a partly sectioned and perspective view, a carrier arm joint or a carrier arm according to the state of the art.

In FIG. 1A a carrier arm joint 10a according to the state of the art is shown, in particular adapted as welded design. A carrier arm 20a is rotatably supported around an axis of rotation D by means of the carrier arm joint 10a on a spindle 4 in a rotary bearing portion 11. The carrier arm joint 10a comprises an adjustment mechanics 12, 13, 14, 15, 16 for adjusting a biasing in the carrier arm 20a.

Two struts 21, 23 of the carrier arm 20a engage with the carrier arm joint 10a. The upper strut comprises a lever bearing 21.1 and a spring 21.2, in particular a compression spring, which exerts pressure on a threaded spindle, which transfers this compression force as traction force to a lever.

The lever bearing 21.1 is adapted as sliding bearing and connects a lever 13 with a spring spindle 21.3. The spring 21.2 generates a counterforce to the weight or mass of a medical device (not shown) which is fastened on an end opposite of the carrier arm joint 10a on the carrier arm 20a. The upper strut 21 may be denoted as spring tube that accommodates a spring assembly and acts as a support of the complete load exerted on the carrier arm by a medical device.

The upper strut 21 is supported on an upper pivot axis 17.1a on the carrier arm joint 10a, and the lower strut 23 is supported on a lower pivot axis 17.2 on the carrier arm joint 10a. This way, a parallelogram-like arrangement may be defined, for which reaction forces are generated in the spring 21.2 and in the lever 13 during pivoting the carrier arm or the medical device upwards or downwards. The lever 13 supports the parallelogram-like arrangement in an additional bearing point, that is, on the support axis or bearing block axis X.

In the following, the adjustment mechanics will be described. A bearing block 12 supports the lever 13 on the carrier arm joint 10a and may introduce spring forces into the carrier arm joint 10a. The bearing block 12 defines the position of the support axis or the bearing block axis X where the lever 13 is supported. A casing 18 of the carrier arm joint and may again specify the different possible positions of the bearing block 12. A distance dz between the bearing block or the bearing block axis X and the pivot axis 17.1a may be adjusted. The maximum possible distance defines an adjustment range Vz which is predetermined by the carrier arm joint. Here, the adjustment range Vz equals a movement range, in which the bearing element 12 or the bearing block or the bearing block axis X may be positioned in a relative distance to the upper pivot axis 17.1a. The adjustment range Vz is also defined by a first stop 19.1, on which the bearing element 12 may abut with a minimum axial distance (pivot axis 17.1, 17.2, and support axis X), and defines a second stop 19.2 positioned opposite to it. Both stops 19.1, 19.2 are here formed by the casing 18 or the carrier arm joint device, but may also be implemented by one or more additional parts. The second stop defines a stop plane E. The setting of the distance dz and thus the payload of the carrier arm may be performed by using adjustment means 14, in particular configured as setscrew. A locking screw 15 may thus mount and secure the adjustment means 14 without play. The bearing block 12 is guided by guiding means, in particular guiding bolts. Primarily, the guiding means 16 accommodate forces that are aligned horizontally. Vertically oriented forces will be forwarded to the adjusting means 14, at least to a considerable extent. Due to a jamming with the guiding means 16, it is not possible to avoid a transfer of also vertical force components to the guiding means 16 at least in parts.

The bearing element 12 comprises a bearing extension 12.2 which protrudes from a central part of the bearing element 12 in a direction opposite to the at least one pivot axis 17.1, 17.2, thus the support axis X is positioned in its position Pmax at the maximum distance from the at least one pivot axis 17.1, 17.2 in the region of the abutment plane E, in particular in the abutment plane E. Here, the abutment plane E is positioned at the maximum distance remote from the at least one pivot axis 17.1, 17.2 in a direction defined by the adjustment range Vz.

The spring biasing of the carrier arm 20 and thus the preload may be set at the factory to the maximum value for the respective (desired) payload range, for example 12 to 18 kg. For this, a mass of the medical device may be taken into account. A fine tuning of the payload is performed by moving the bearing block 12 or the bearing block axis X within the adjustment range Vz, that is from the (depicted) top position downwards to the upper pivot axis 17.1a. The movement is performed by turning a setscrew 14. Depending on the direction of rotation of the setscrew 14, the bearing block 12 goes up or down and thus changes the angle of the lever 13 and thus an effect caused by the spring 21.2.

In the upper position of the bearing block 12 (maximum distance dz, Pmax) the carrier arm 20 may then accommodate the maximum load of 18 kg for example, and in the lower position of the bearing block 12 (dz=0), that is in a position adjacent to the upper pivot axis 17.1a only the minimum load, for example 12 kg, is supported. The bearing block 12 may thus not be guided past the upper pivot axis 17.1a, but only to a position adjacent to the pivot axis. In this range of the spring biasing preset at the factory it is not possible to set payloads smaller than the said 12 kg, that are described here as example. In order to enable smaller payloads, a different spring biasing has to be preset at the factory or also another spring 21.2 is required.

Figure 1B:
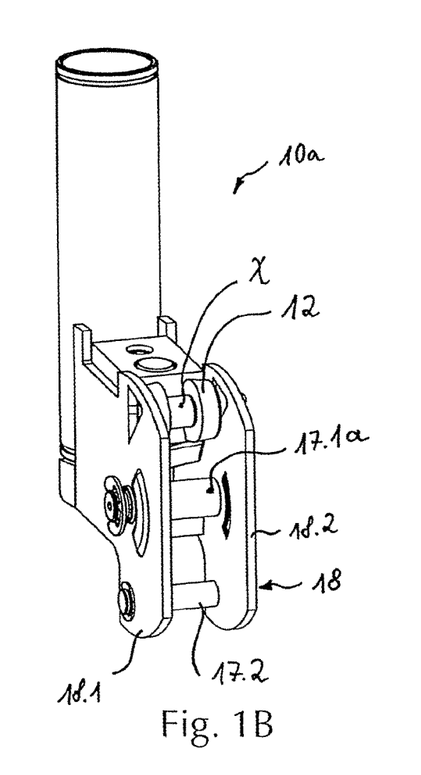

In FIG. 1B the arrangement of the support axis or of the bearing block axis X in relation to the upper pivot axis 17.1a is shown. Here the upper pivot axis 17.1a extends along the complete length between two outer casing walls 18.1, 18.2 of the carrier arm joint.

Figure 2A:
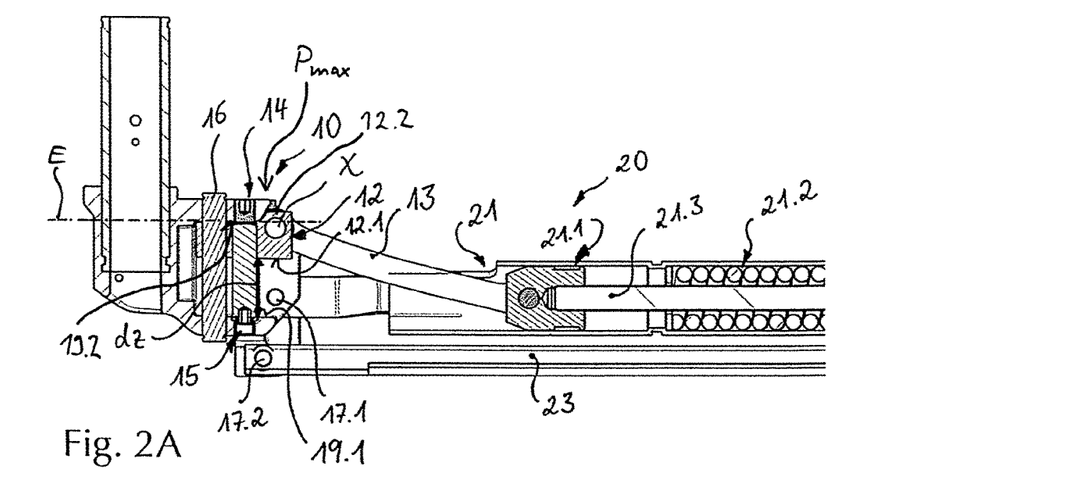
In FIG. 2A, 2B, 2C in a partly sectioned and perspective view, a carrier arm joint device or a carrier arm device according to an exemplary embodiment of the invention, wherein a bearing element is arranged in an upper position.
Figure 2B:
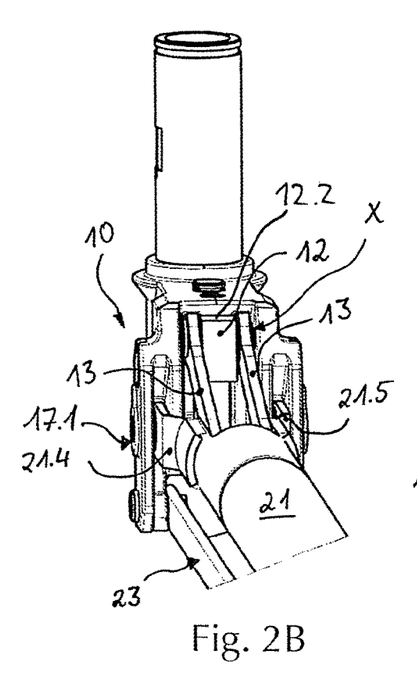
Figure 2C:
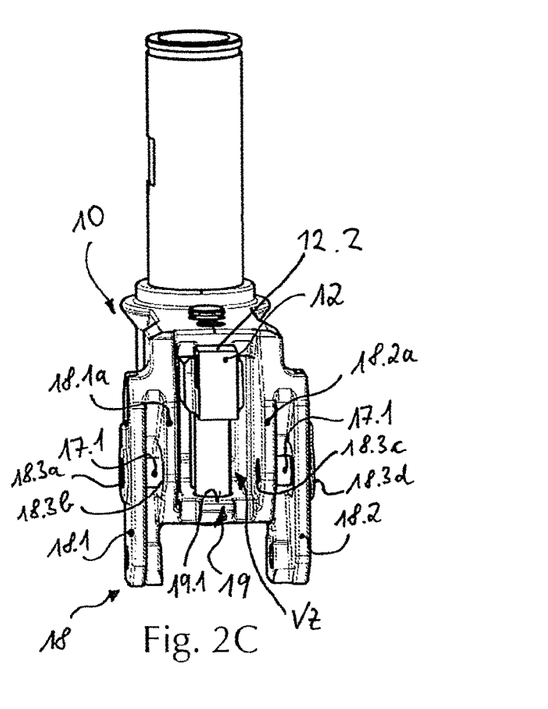

In the FIGS. 2A, 2B, 2C a carrier arm joint device 10 is shown, which provides a comparatively large adjustment range for the support axis or the bearing block axis X and thus a large adjustment range for payloads. A spring 21.2, in particular a compression spring, creates biasing forces which are transferred to the lever 13 via the spring spindle 21.3 as traction forces. For this end, the compression spring may be biased between two points in the spring tube 21. On a side facing the carrier arm joint device 10, forces are exerted against a constriction in the spring tube and on the opposite side forces are exerted against the threaded spindle 21.3, which passes through the spring 21.2, and onto which a biasing nut is screwed to set (in particular factory-set) of the biasing, as shown in FIG. 5B. This way, a traction force may be exerted by using the compression spring 21.2 to the threaded spindle 21.3, which is transferred via the lever bearing and the lever to the bearing element/the bearing block 12.

Also in this exemplary embodiment, the adjustment range Vz is defined by a first stop 19.1, on which the bearing element 12 may abut with a minimum distance between the axes (pivot axis 17.1, 17.2, and support axis X) and a second stop 19.2 that is positioned opposite thereto. Both stops 19.1, 19.2 are formed by the casing 18 or the carrier arm joint device in the present exemplary embodiment, but may also be implemented by one or more additional parts. The second stop defines an abutment plane E. The bearing element 12 again comprises a bearing extension 12.2 which protrudes from a central part of the bearing element 12 in a direction opposite to the at least one pivot axis 17.1, 17.2, thus the support axis X is positioned in its position Pmax at the maximum distance from the at least one pivot axis 17.1, 17.2 in the region of the abutment plane E, in particular in the abutment plane E. Here, the abutment plane E is positioned at the maximum distance remote from the at least one pivot axis 17.1, 17.2 in a direction defined by the adjustment range Vz.

The carrier arm joint device 10 is formed as cast part, in particular made from aluminum. The cast casing 18 comprises also tongues 18.1a, 18.2a in addition to the walls 18.1,

18.2. The upper pivot 17.1 does not completely extend between the walls 18.1, 18.2, but is partitioned into two individual, separate portions, which extend between one of the walls 18.1, 18.2 and a corresponding tongue 18.1a, 18.2a, respectively. Each portion of the pivot axis is only supported in one of the walls 18.1, 18.2. Each portion of the pivot axis is supported in the corresponding tongue 18.1a, 18.2a.

Also in this arrangement, the payload of the carrier arm may be set by moving the bearing block 12 along the guiding bolt 16 by means of the setscrew 14. However, a maximum adjustment range Vz may be provided, and the carrier arm is thus configured for a broader payload spectrum. Hereto, the upper pivot axis 17.1 is adapted as partitioned axis. This way, the bearing block 12 may be moved in the lower position between the single portions/parts of the axis 17.1 without clashing with the axis 17.1. In the embodiment shown, the movement range of the bearing block 12 is possibly only limited by the inner contour of the carrier arm joint 20. The bearing block 12 may be moved across a comparatively large adjustment arrange Vz and thus ensure a comparatively large range for setting the payload. This enables, for example with a factory setting of the spring biasing set to the maximum of for example 21 kg, to directly set or readjust the payload range of the carrier arm between 1.5 kg and 21 kg, for example, by means of the adjustment means 14 on-site.

In FIG. 2A the distance dz is at its maximum. The securing element 12 is arranged in a top position.

The arrangement of the setscrew 14 between the guiding bolt 16 and the support axis X may ensure an advantageous stress distribution in the cast casing 18.

The alignment of the setscrew 14 and of the guiding bolt 16 is vertically or orthogonally to the struts 21, 23 aligned in the horizontal direction. This way, an especially large pivot range of the carrier arm device 20 may be provided. The kinematics of the parallelogram-like carrier arm 20 may here advantageously be coupled to the carrier arm joint device. In addition, in this vertical alignment of the setscrew 14 and the guiding bolt 16, the carrier arm joint device 10 may be performed in a simple way.

The achievable pivot range is, from the horizontal arrangement, for example to 45° upwards and to −70° downwards.

The carrier arm joint 10 may for example be adapted as an aluminum cast design. The configuration as a cast part has the advantage of a comparatively simple, robust mounting of both portions of the upper pivot axis 17.1. The cast casing 18 may also be provided with a high torsional strength and rigidity, also for a partitioned pivot axis 17.1. However, a welded construction would have to be supported in a complex way.

In FIG. 2B is shown that the upper strut 21 comprises two extensions 21.4, 21.5 which are supported separately on one of the separate axial portions of the upper pivot axis 17.1, respectively, in particular between two casing extensions, respectively.

As shown in FIG. 2C, the casing 18 defines 4 bearing points 18.3a, 18.3b, 18.3c, 18.3d, wherein each half axis or each axial portion of the upper pivot axis 17.1 is supported in two of the bearing points. The bearing points 18.3a, 18.3b, 18.3c, 18.3d may form a transition fit in combination with the respective axis portion.

Further, in FIG. 2C an adjustment range Vz is shown, which extends downwards to a stop 19 on the casing 18. The bearing block 12 may abut on a planar abutment surface 19.1 (lowest position).

Figure 3A:
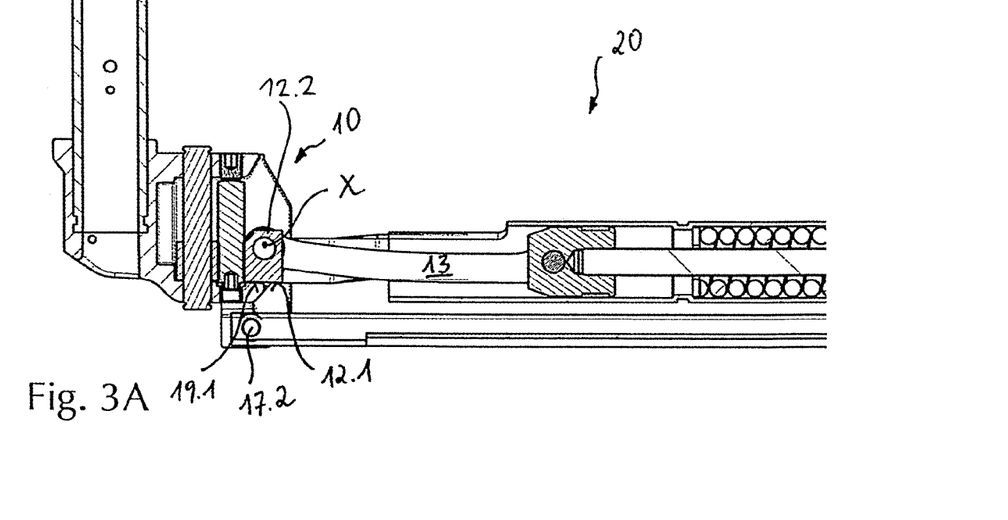
In FIG. 3A, 3B, 3C in a partly sectioned and perspective view, a carrier arm joint device or a carrier arm device according to an exemplary embodiment of the invention with a bearing element in a lower position.
Figure 3B:
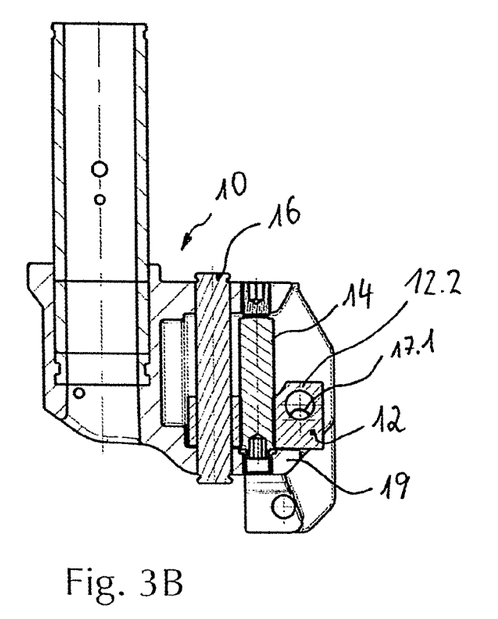
Figure 3C:
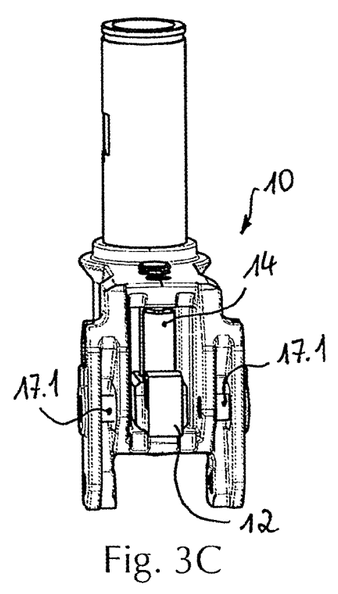

In FIG. 3A, 3B, 3C a bearing element 12 or the support axis X is shown in a bottom position, corresponding to the smallest possible payload of the carrier arm device 20. The planar lower side 12.1 of the bearing element 12 abuts on the planar surface portion 19.1 of the casing 18 or the stop 19. The distance Dz is 0. As can be seen in FIG. 3B, the arrangement of the bearing element 12 is independent of the position of the upper pivot axis 17.1. The bearing element 12 is guided past the pivot axis 17.1 and overlaps with it. Then, the support axis is arranged almost at the height of the pivot axis 17.1. Optionally the support axis may also be arranged further downwards, but here the effect of the spring is more and more weakened.

Figure 4:
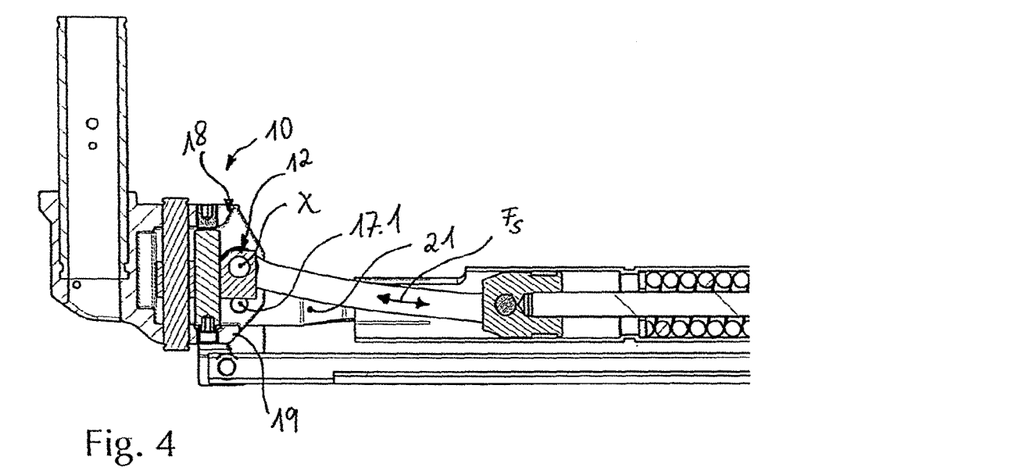
In FIG. 4 in a partly sectioned view, a carrier arm device with a carrier arm joint device according to an exemplary embodiment of the invention with the bearing element in a centered position; and In FIG. 5A, 5B in a partly sectioned and perspective view components of the stand device with a medical device, a carrier arm device, and a carrier arm joint device according to an exemplary embodiment of the invention.

In FIG. 4 a centered position of the support axis X in the center of the adjustment range Vz is shown. The bearing block 12 is arranged at least approximately in the center between the lower stop 19 and a corresponding upper stop in the casing 18. The bearing block 12 or the support axis X may be arranged independent of the position of the upper pivot axis 17.1. Holding forces FS, in particular traction forces, may be transferred to the lever 13, thus the carrier arm 20 may be stabilized in a desired orientation, for example horizontally. In the arrangement of the lever 13 shown, a force FS with a predefined amount causes a middle impact as the lever arm between the support axis X and the upper pivot axis 17.1 is set to a middle value.

Figure 5A:
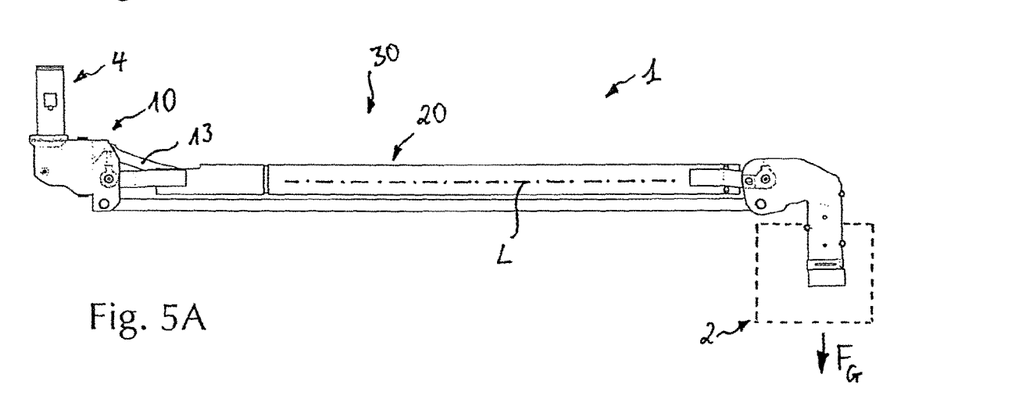
Figure 5B:
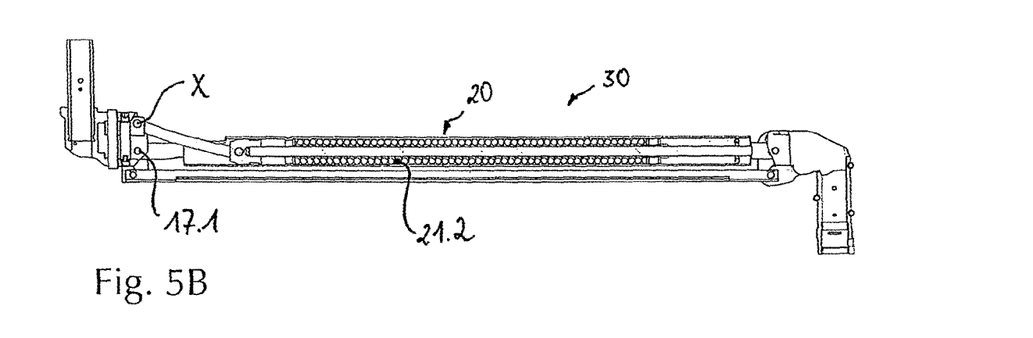

In the FIGS. 5A, 5B single components of the stand device 1 are shown, comprising a medical device 2, a carrier system 30 with at least one carrier arm 20 extending along a longitudinal axis L and at least one carrier arm joint device 10 and a spindle or a pin 4.

The medical device 2 exerts a weight FG, which is a taken up via the lever 13 and the support axis in the carrier arm joint device 10, and is transferred to the spindle 4. In the shown arrangement of the support axis X with a maximum distance dz relative to the upper pivot axis the highest payload may be supported. The spindle 4 may be supported in a bushing or a ceiling flange, for example.

The invention may be summarized as follows. A payload of the carrier arm joint or a carrier system may be set over a broad spectrum such that a support axis of the carrier arm joint is arrangeable independent of the position of a pivot axis in relation to this pivot axis in a predefinable distance or with a predefined lever, in particular in a comparatively small distance. The support axis may be arranged in a support element or bearing block, and the support element may be moved past the pivot axis, thus the supporting element may be geometrically configured and arranged independent of the position of the pivot axis. Such a carrier arm joint may be formed in an especially stable, rigid, and robust way and may provide a maximum adjustment range in relation to the dimensions of the carrier arm joint. Finally, a broad payload spectrum may be covered with a comparatively small, compact and carrier arm joint having a high structural rigidity. This enables, for example, to reduce the number of variants for this carrier arm joint.

LIST OF REFERENCE NUMBERS

1 Stand device, in particular ceiling stand device
2 Medical device
4 Spindle or pin
10a State of the art carrier arm joint
10 Carrier arm joint device
11 Rotary bearing portion
12 Bearing element/supporting element, in particular bearing block 12.1 Planar lower side of the bearing element
12.2 Bearing extension of the bearing element/bearing block
13 Lever
14 Adjustment means, in particular setscrew
15 Locking screw
16 Guiding means, in particular guiding pin
17.1, 17.2, 17.1a Pivot axis for strut
18 Casing
18.1; 18.2 Casing wall
18.1a, 18.2a Casing tongue
18.3a, 18.3b, 18.3c, 18.3d Bearing points on the casing
19 Stop or step or protrusion
19.1 Planar surface portion of the stop
19.2 Second stop
20a State of the art carrier arm
20 Carrier arm device (spring arm, cantilever)
21 First strut, in particular spring tube
21.1 Lever bearing in first strut
21.2 Spring
21.3 Spring spindle
21.4; 21.5 Strut extension
23 Second strut
30 Carrier system
dz Adjustable distance between the bearing block and the pivot axis
D Axis of rotation for spindle, in particular vertically aligned height axis
E Stop plane (of the second stop)
FG Weight of the medical device
FS Holding force (traction or compression force)
L Longitudinal axis of the carrier arm
Vz Adjustment range
X Support axis or bearing block axis The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A carrier arm joint device for a carrier arm of a stand device for arranging in an operating room and for displacing a medical device held on the carrier arm, wherein the carrier arm joint device is configured for setting a payload corresponding to a weight of the medical device to be supported by the carrier arm, the carrier arm joint device comprising:
at least one pivot axis for mounting at least one strut of the carrier arm;
a support axis to support a lever configured to transfer forces holding the carrier arm between the strut and the carrier arm joint device;
a casing having a first stop that defines a first abutment plane and a second stop, opposite to the first stop, the second stop defining a second abutment plane;
a bearing element including a bearing block that defines a position of the support axis, the bearing element moveably coupleable to the lever via the support axis;
wherein the bearing block is moveable between the first and second abutment planes, the second abutment plane axially positioned below the at least one pivot axis a distance that is adjustable within an adjustment range in order to set the payload.

2. The carrier arm joint device according to claim 1, wherein the at least one pivot axis is arranged relative to the support axis such that the at least one pivot axis and the support axis do not overlap in an axial direction.

3. The carrier arm joint device according to claim 1, wherein the at least one pivot axis is partitioned in portions, the portions being spaced apart from a region in which the bearing block moves, the region being sized and shaped to allow the bearing block to move independent of a position of the at least one pivot axis.

4. The carrier arm joint device according to claim 1, wherein the at least one pivot axis is partitioned in at least two partitions, the at least two partitions spaced apart to define a cavity which is centered in the carrier arm joint device, wherein the adjustment range is arranged in the cavity, the cavity sized and shaped to receive therein the lever, the lever positioned between the at least two partitions.

5. The carrier arm joint device according to claim 1, further comprising:
an adjustment member for adjustably setting the distance in the adjustment range, the adjustment member coupleable to the bearing element.

6. The carrier arm joint device according to claim 5, wherein the adjustment member is configured to guide the bearing element past the at least one pivot axis.

7. The carrier arm joint device according to claim 1, wherein at least one separate portion of the at least one pivot axis is separately supported in a casing wall and a corresponding casing tongue.

8. The carrier arm joint device according to claim 1, further comprising a guiding member configured to guide the bearing element defining the support axis along a predefined movement path in the adjustment range, the movement path providing a straight movement path, wherein the guiding member is provided for adjustment of an axial distance positioned between the guiding member and the at least one pivot axis.

9. The carrier arm joint device according to claim 1, wherein the carrier arm joint device is a cast part made from aluminum.

10. The carrier arm joint device according to claim 1, wherein a bearing extension protrudes outwardly from a central part of the bearing element relative to the at least one pivot axis.

11. A stand device for arranging in the operating room and for displacing at least one medical device in an operating room, comprising at least one of the carrier arm joint device according to claim 1 or at least one carrier system according to claim 10.

12. A carrier system for a stand device for arranging in an operating room and for displacing a medical device having a predefined mass, the carrier system comprising:
at least one carrier arm for holding a medical device with at least one strut; and
at least one carrier arm joint device, including:
at least one pivot axis for mounting the at least one strut of the carrier arm;

a support axis to support a lever configured to transfer forces holding the carrier arm between the strut and the carrier arm joint device;

a casing having a first stop that defines a first abutment plane and a second stop, opposite to the first stop, the second stop defining a second abutment plane; and a bearing element including a bearing block that defines a position of the support axis, the bearing element coupleable to the lever via the support axis;

wherein the bearing block is moveable between the first and second abutment planes, the second abutment plane axially positioned fully below the at least one pivot axis a distance that is adjustable within an adjustment range for setting a payload of the carrier arm joint device in relation to the predefined mass to be held.

13. The carrier system according to claim 12, wherein the strut of the carrier arm is supported in two separate portions of the at least one pivot axis, wherein the portions are supported in the casing of the carrier arm joint device, and wherein the adjustment range is laterally limited by the casing.

14. The carrier system according to claim 12, wherein the carrier arm is adapted as a parallelogram-like carrier arm, and wherein the carrier arm joint device defines two pivot axes, and wherein the support axis is arranged above both pivot axes.

15. A usage of the carrier arm joint device for setting a payload of a medical carrier system, the carrier arm joint device comprising:

at least one pivot axis for mounting at least one strut of the carrier arm;

a support axis to support a lever configured to transfer forces holding the carrier arm between the strut and the carrier arm joint device;

a casing having a first stop that defines a first abutment plane and a second stop, opposite to the first stop, the second stop defining a second abutment plane;

a bearing element including a bearing block that defines a position of the support axis, the bearing element coupleable to the lever via the support axis;

wherein the bearing block is moveable between the first and second abutment planes, the second abutment plane axially positioned fully below the at least one pivot axis a distance that is adjustable within an adjustment range in order to set the payload.

* * * * *